(12) United States Patent
Yokota et al.

(10) Patent No.: US 6,254,749 B1
(45) Date of Patent: *Jul. 3, 2001

(54) CARBON MONOXIDE GAS SENSOR AND MEASURING DEVICE USING THE SAME SENSOR

(75) Inventors: Minoru Yokota, Nagoya; Takao Murase, Konan; Junichiro Mizusaki, Sebdai, all of (JP)

(73) Assignee: NGK Insulators, Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,346

(22) Filed: Dec. 19, 1997

(30) Foreign Application Priority Data

Dec. 27, 1996 (JP) .................................................. 8-351449
Dec. 1, 1997 (JP) .................................................. 9-330501

(51) Int. Cl.[7] ............................................... G01N 27/407
(52) U.S. Cl. .................... 204/424; 204/425; 204/426; 204/427; 205/784.5
(58) Field of Search ................................ 204/421–429; 205/783.5, 784, 784.5, 785

(56) References Cited

U.S. PATENT DOCUMENTS

| | | | |
|---|---|---|---|
| 3,843,400 | * 10/1974 | Radford et al. | 204/421 |
| 4,190,499 | * 2/1980 | Pebler | 205/784.5 |
| 4,225,634 | * 9/1980 | Tanaka et al. | 204/428 |
| 4,264,425 | * 4/1981 | Kimura et al. | 204/425 |
| 4,502,939 | * 3/1985 | Holfelder et al. | 204/425 |
| 4,626,337 | * 12/1986 | Hotta et al. | 204/429 |
| 4,828,673 | * 5/1989 | Maeda | 204/427 |
| 5,366,611 | * 11/1994 | Ioannou et al. | 204/426 |
| 5,397,442 | * 3/1995 | Wachsman | 204/781 |
| 5,472,580 | * 12/1995 | Kennard et al. | 205/784.5 |
| 5,672,811 | * 9/1997 | Kato et al. | 204/425 |
| 5,716,507 | * 2/1998 | Tanaka et al. | 204/424 |
| 5,736,028 | * 4/1998 | Hjortsberg et al. | 204/424 |

FOREIGN PATENT DOCUMENTS

| | | |
|---|---|---|
| 0 468 249 | 1/1992 | (EP) . |
| 4-14302 | 3/1992 | (JP) . |
| 4-208849 | 7/1992 | (JP) . |
| 7-248309 | 9/1995 | (JP) . |
| 8-189914 | 7/1996 | (JP) . |
| WO 86/06168 | 10/1986 | (WO) . |

\* cited by examiner

*Primary Examiner*—T. Tung
(74) *Attorney, Agent, or Firm*—Parkhurst & Wendel, L.L.P.

(57) ABSTRACT

In a CO gas sensor composed of a CO gas sensing electrode 3 being made of Au or an Au alloy and a reference electrode 2 electrically connected to at least part of a surface of a solid electrolyte having an oxygen ion transfer property, which is superior in CO gas selectivity, in particular, reducing the affect of the co-existing oxygen to CO, and which works with a high precision at a high temperature, and in a CO gas measuring device using the gas sensor, the gas sensor being capable of determining a CO gas concentration by measuring a electromotive force change due to adsorption/oxidization of the carbon monoxide gas in the sensing electrode 3 when a constant current is caused to flow between the reference electrode 2 and the sensing electrode 3 or a current value caused by the oxidizing reaction of the carbon monoxide gas in the sensing electrode when a voltage is kept constant between the reference electrode 2 and the sensing electrode 3.

33 Claims, 12 Drawing Sheets

CO CONCENTRATION-CURRENT VARIATION
CHARACTERISTICS UNDER CONSTANT VOLTAGE

CO CONCENTRATION-VOLTAGE VARIATION CHARACTERISTICS
UNDER APPLICATION OF CONSTANT CURRENT

CARBON MONOXIDE GAS SENSOR AND MEASURING DEVICE USING THE SAME SENSOR

BACKGROUND OF THE INVENTION

1. Field of the Invention

The present invention relates to a CO gas sensor for measuring a concentration of carbon monoxide (CO) gas contained in air or an exhaust gas from a combustion engine or the like and a CO gas concentration measuring apparatus using said CO gas sensor, and more particularly to a CO gas sensor that is operatable at a high temperature of 600 to 900° C. with reducing an adverse affect of coexistence oxygen ($O_2$) to a CO gas measurement value, and a CO gas concentration measuring apparatus using said CO gas sensor.

2. Related Art Statement

There are many poisoning and fatal accidents caused by CO gas generated by an incomplete combustion in an apparatus for burning fossil fuel, i.e., heater equipment such as a petroleum stove, a petroleum or oil fan heater, a gas heater or a hot water supplying equipment for heating water. This is because the human being can not notice the generation of the CO gas since CO gas has no color and no smell. Also, in a room or the like in which the above-described equipment is installed, since CO gas is a gas having substantially the same molecular weight as that of air, CO gas is diffused uniformly in the air. As a result, the human being unconsciously inspires CO gas, so that the inspired CO gas is combined directly with hemoglobin in the blood. In this case, he or she can not continue the inspiration of oxygen to cause a suffocation.

On the other hand, as described above, CO gas is a harmful gas to the human body but is useful in the industrial field. For example, methanol is synthesized from hydrogen ($H_2$) gas and CO gas and used as material for various chemical products.

It is desired to reduce the concentration of CO gas discharged from an internal combustion engine or a combustion furnace for reasons of various regulations on the components in exhaust gas and a more effective use of fossil energy resources which are derived from recent environmental problems. For this reason, the composition of an exhaust gas is analyzed so as to optimize the combustion efficiency and the operation conditions by, for example, feeding back and processing the exhuast gas. Also, the on-site tests and researches of a power generating system using a fuel cell having a higher energy conversion efficiency than that of a conventional power generating system using a turbine have steadily progressed. In such a fuel cell, a mixture gas of CO gas and hydrogen ($H_2$) gas produced by reacting water steam under the presence of catalyst or a commercial gas mainly composed of methane ($CH_4$) is used as fuel.

As described above, a variety of combustion equipments requires installation of sensors for measuring a concentration and detecting the generation of CO gas. Also, the maintenance and investigation of these combustion equipments requires portable CO gas concentration measurement devices. Also, in a chemical plant or a combustion engine or the like, it is preferable to always monitor a CO gas concentration for controlling suitably the CO gas concentration.

Main kinds of such CO gas sensors are classified into a semiconductor type, a catalyst combustion type, a solid electrolyte type and a thermal transfer type. Among those, the solid electrolyte type CO gas sensor is based upon the measurement principle, i.e., the electromotive force measurement for a rich/lean cell, is composed of a metal electrode and a stabilized zirconia having an oxygen ion transfer property, and is superior in heat resistance, shock resistance and poisoning resistance.

However, since the CO gas sensor using the stabilized zirconia is also an oxygen sensor, it is difficult to selectively measure a CO gas concentration in a gas in which oxygen coexists. Also, in a sensor using a platinum electrode which is used in general, the oxidation of CO gas is rapid on the platinum electrode surface at such a high temperature of 600 to 900° C.

Therefore, it is difficult to distinguish the measurement results attributed to oxygen and CO gases, in the case where oxygen is contained in a gas to be measured respectively.

SUMMARY OF THE INVENTION

In view of the foregoing defects, an object of the present invention is to provide a CO gas sensor for suitably measuring a concentration of CO gas contained in a gas containing oxygen, and a CO gas concentration measuring device using the CO gas sensor. Namely, according to the present invention, there are provided a carbon monoxide gas sensor having a solid electrolyte having an oxygen ion transfer property, and carbon monoxide gas measurement sensing and reference electrodes electrically connected to at least part of the surface of the solid electrolyte, characterized in that gold or gold alloy is used in the sensing electrode and an apparatus for measuring the concentration of CO gas equipped with said gas sensor.

Also, according to the present invention, there is provided a carbon monoxide gas sensor comprising: a solid electrolyte having an oxygen ion transfer property; carbon monoxide gas measurement sensing and reference electrodes electrically connected to at least part of the surface of the solid electrolyte; and oxygen measurement sensing and/or reference electrodes; wherein gold or gold alloy is used in the carbon monoxide gas measurement sensing electrode. Also, a carbon monoxide gas concentration measuring apparatus equipped with said gas sensor is provided.

Thus, by the CO gas sensor according to the present invention, in the case where the concentration of CO gas in the air or an exhaust gas emitted from the combustion engine is to be measured, Au or Au alloy that has a lower catalyst property than that of Pt having conventionally been used is used in the sensing electrode for measurement of CO gas, whereby it is possible to enhance the selectivity of CO gas. Also, CO gas measurement value is compensated by an oxygen measurement value by using an oxygen sensor, whereby it is possible to enhance the CO gas measurement precision. Furthermore, it is advantageous that the adverse affect of the oxygen concentration to the CO gas concentration measurement value can be extremely suppressed by using jointly an oxygen pump. In addition, in all of the embodiments of the CO gas sensors according to the present invention, it is possible to enhance the sensitivity to CO gas in the CO gas sensing electrode by causing the constant current to flow between the CO gas measurement electrodes or keeping the constant voltage therebetween. In general, it is possible to considerably enhance the measurement precision of the CO gas sensors. The surface of a solid electrolyte to be connected to a sensing electrode is chemically etched to be roughed or a fine particle layer made of Au or Au alloy is formed between a solid electrolyte and a electrode film so as to increase the area of a contact interface among a gas phase, a metal electrode and a solid electrolyte to thereby further enhance the CO gas detecting sensitivity. Furthermore, the sensor operates at such a high temperature of 600 to 900° C. and it is advantageous that an error by the other interference gases included in the measurement gas can be reduced. Also, a high temperature pre-treatment portion, i.e., a heater is provided for preheating a gas to be measured so as to obviate the adverse affect caused by NO or $SO_2$, thereby a further enhance in the precision of the carbon monoxide concentration can be achieved.

PREFERRED EMBODIMENTS OF THE INVENTION

Figure 1:
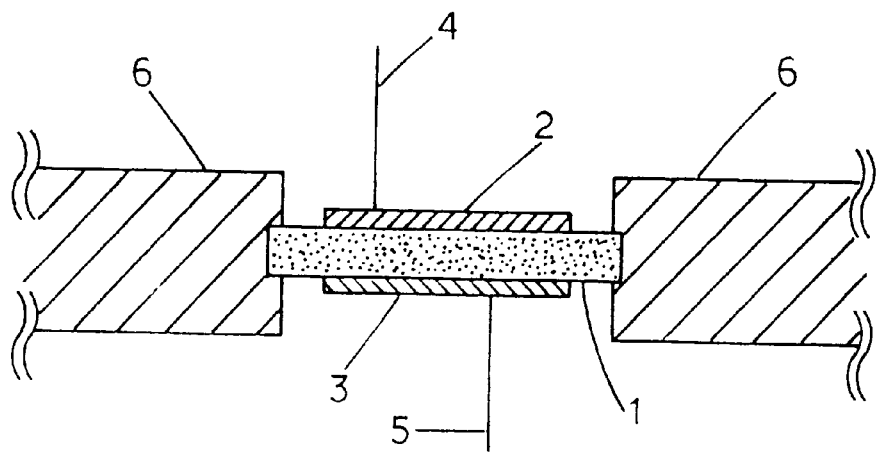
FIG. 1 is a cross-sectional view showing a basic structure of a CO gas sensor according to the present invention.

According to the present invention, there is provided a carbon monoxide gas sensor comprising: a solid electrolyte having an oxygen ion transfer property; carbon monoxide gas measurement sensing and reference electrodes electrically connected to at least part of the surface of the solid electrolyte; oxygen measurement sensing and/or reference electrodes; and optionally an oxygen pump cell for controlling an oxygen concentration in the measurement atmosphere, wherein gold or gold alloy is used in the carbon monoxide gas measurement sensing electrode. Moreover, it is preferable that the electrode used in the oxygen pump cell installed in the carbon monoxide gas sensor is a metal oxide electrode which does not oxidize carbon monoxide.

In the above-described carbon monoxide gas sensor, a carbon monoxide gas measurement sensing electrode can be a cermet electrode made of a mixture of gold or gold alloy and the same material as that of the solid electrolyte, and it is preferable to provide a gas diffusion regulating layer on the surface of the sensing electrode. In particular, in the case where combustible gas having a high molecular weight such as a high hydrocarbon such as propane, butane or hexane is contained in a measurement gas, it is preferable to use a sensor having a gas diffusion regulating layer. Also, as a sensor structure, it is possible to take the structure in which both the carbon monoxide gas measurement sensing and reference electrodes are disposed on the same surface of the solid electrolyte. Furthermore, it is possible to take the structure in which an auxiliary reference electrode for carbon monoxide gas measurement is provided in addition to the carbon monoxide gas measurement sensing and reference electrodes to form a three-electrode structure.

In the case of the carbon monoxide gas sensor according to the present invention, it is possible to employ a method in which an electromotive force change caused by the adsorption and oxidization of carbon monoxide in the sensing electrode, with applying a constant current between the carbon monoxide gas measurement sensing and reference electrodes, is measured so as to determine the concentration of carbon monoxide gas. It is thus possible to enhance the measurement sensitivity of the carbon monoxide. Otherwise, a current value caused by the oxidization of carbon monoxide gas in the sensing electrode when a constant voltage is maintained between the carbon monoxide gas measurement sensing and reference electrodes is measured so as to determine the concentration of carbon monoxide gas with a high sensitivity in good condition.

In particular in the case where gas such as NOx or SOx is contained in a gas to be measured, a high temperature pre-treatment portion for preheating gas to be measured in the range of 850 to 950° C. can be provided in a part of the gas flow path before the gas reaches a carbon monoxide gas sensing electrode, in the flow path provided for introduction and discharge of the gas to be measured in the carbon monoxide gas sensor. Since NOx gas or SOx gas reaches the chemical equilibrium (NO←→$NO_2$, $SO_2$←→$SO_3$) at the vicinity of sensor temperature in the pre-treatment portion, the interference of the carbon monoxide gas sensing electrode with NO gas or $SO_2$ gas can be reduced with such an arrangement.

Furthermore, in the carbon monoxide gas sensor provided with the oxygen gas measurement electrode in addition to the carbon monoxide measurement electrode, such a method can be adapted that a carbon monoxide concentration and an oxygen concentration are simultaneously measured, and the measurement result of carbon monoxide is compensated for by the measurement result of the oxygen concentration so as to determine the carbon monoxide gas concentration. Also, in the case where an auxiliary reference electrode is added to the carbon monoxide measurement electrode, constant current is applied between a carbon monoxide gas measurement sensing electrode and a reference electrode to measure the voltage between auxiliary reference electrode and the sensing electrode, or a constant voltage is maintained between the sensing electrode and the reference electrode to measure an electric current between the sensing electrode and the auxiliary reference electrode to thereby determine carbon monoxide concentration with separating only CO gas reaction, with a high precision. It is therefore possible to enhance the measurement precision by applying above-described measuring methods in combination in compliance with the structure of the present carbon monoxide gas sensor.

It is preferable that the solid electrolyte that is one of components of the carbon monoxide gas sensor is made of zirconium oxide and stabilizer. It is preferable that the stabilizer included in the solid electrolyte is at least one member selected from the group consisting of magnesium oxide, calcium oxide, yttrium oxide, cerium oxide, scandium oxide, and rare earth metal oxides. It is also preferable that the electrodes other than the carbon monoxide gas measurement sensing electrode are cermet electrodes made of a mixture of porous platinum or platinum and the same material as that of the solid electrolyte. Furthermore, in the case where the solid electrolyte can be heated and kept at a constant temperature in the range of 600 to 900° C. by providing a temperature measurement element and a heater at the vicinity of or integrally with the solid electrolyte, it is possible to cope with the reduction of the temperature dependence of the measurement value.

Figure 12:
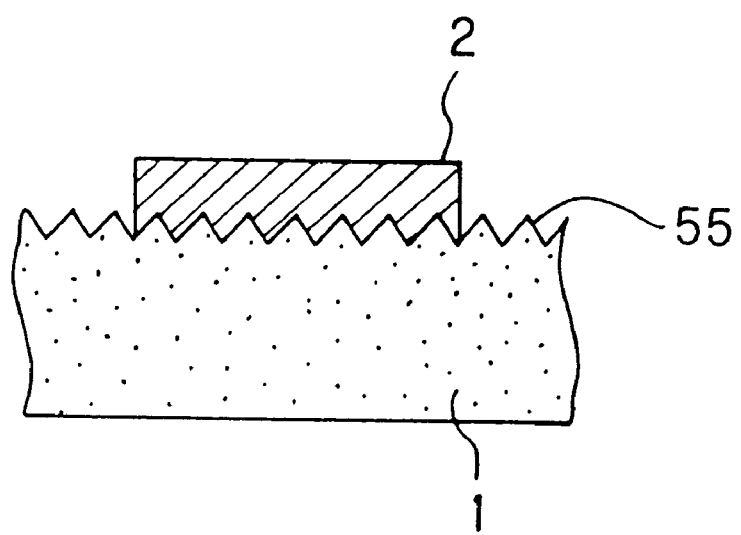
FIG. 12 is a cross-sectional view schematically showing a joint condition between a solid electrolyte and an oxygen gas sensing electrode in an oxygen gas sensor according to the present invention in which the CO gas sensing electrode is formed on the surface of the solid electrolyte that has been roughed on the joint side with the CO gas sensing electrode.

It is preferred to enhance the contactability between a solid electrolyte and a carbon monoxide gas measurement sensing electrode, and increase simultaneously the area of the contact interface among the sensing electrode, the solid electrode and CO gas by etching in advance the surface of the solid electrolyte, for example, by etching chemically as illustratively shown in FIG. 12 when the sensing electrode is formed on the solid electrolyte.

Instead of the above-described etching treatment, it is possible to obtain the same effect by disposing on the solid electrolyte a layer made of Au or Au alloy fine particles having a specific average particle size and laying an electrode film on the fine particle layer.

According to the present invention, the above-described carbon monoxide gas sensor is used as a direct insertion type sensor inserted into the measurement atmosphere as disclosed in Japanese Patent Application Laid-Open No. 1-250753, or as a direct coupling type sensor disposed close to the measurement atmosphere as described in Japanese Patent Application Laid-Open No. 3-277957 for introducing the measurement gas into the device by utilizing the flow of the measurement gas for measuring the concentration of the gas component of the combustion gas. Thus, it is possible to measure a carbon monoxide concentration with a higher precision. It is therefore possible to feed back the data for more complete combustion to enhance the combustion efficiency.

As described above, according to the present invention, in the case where carbon monoxide gas contained in the air or an combustion engine is measured, Au or Au alloy having a lower catalyst property than that of Pt having conventionally been employed is used in the sensing electrode for measurement of CO gas; whereby it is possible to suppress the affect of the oxygen concentration on the CO gas concentration measurement. Furthermore, there is provided an advantage that the present sensor can be operable at such a high temperature of 600 to 900° C. by doing so.

Also, a constant current is caused to flow between a CO gas measurement sensing electrode and a reference electrode or a constant voltage is kept between the sensing and reference electrodes, whereby the oxidation of CO gas is accelerated within the sensing electrode and the sensitivity of the CO gas sensor to CO gas can be enhanced.

The embodiments of the present invention will now be described with reference to the accompanying drawings. It is however understood that the present invention is not limited to theose embodiments FIG. 1 is a cross-sectional view showing a basic structure of a CO gas sensor according to the present invention. A pair of electrodes, i.e., a reference electrode 2 and a sensing electrode 3 are formed on surfaces of a solid electrolyte plate 1 so that the latter is sandwiched by the pair of electrodes. In this case, the reference electrode 2 is formed on the side of the reference gas and the sensing electrode 3 is formed on the side of the gas to be measured. Lead lines 4 and 5 are connected to the respective electrodes. Also, the solid electrolyte plate 1 is inserted into a base 6 and serves as a partition wall between the measurement gas region and the reference gas region.

It is possible to use as a material of the solid electrolyte plate I a material having an oxygen ion transfer property. It is possible to enumerate zirconium oxide, bismuth oxide, cerium oxide and the like. However, according to the present invention, it is preferable to use a "stabilized zirconia" that is superior in high temperature stability and chemical stability. The "stabilized zirconia" means a material as defined below: The pure zirconium oxide causes a martensite type phase transition accompanying a volume change between a monoclinic system and a tetragonal system at about 1000° C. In this phase transition, a crack is generated. Accordingly, in order to prevent this, a metal oxide of two-equivalence or three-equivalence which is called as a stabilizing material is solid-molten so that the tetragonal system which is the stabilized phase of the zirconium oxide at a high temperature is made the stabilized phase in the entire temperature range. Also, the solid melt of such a stabilized material causes the oxygen deficiency and also serves to enhance the ion transfer degree. According to the present invention, as a stabilizing material, it is possible to use magnesium oxide (MgO), calcium oxide (CaO), yttrium oxide ($Y_2O_3$), cerium oxide ($CeO_2$), scandium oxide ($Sc_2O_3$) and rare earth oxides.

Also, as a method of producing the solid electrolyte plate 1, it is possible to use a variety of kinds of conventional methods such as a press molding method, a casting method, or an extruding molding method or a pressing method of pressing a green sheet produced by a doctor blade method to obtain a molded article having a desired shape. This is degreased and baked for a final product. It is possible to employ further a polishing and cutting process therein if necessary. Also, it is possible to use a roughing method for the surfaces by dipping it in a chemical etching liquid for example, such as a 2.5% fluorine acid solution for 20 to 30 minutes.

Next, the reference electrode 2 is used for being electrically connected to the solid electrolyte plate 1 and requires the function as the electrode for diffusing/adsorbing the gas. It is therefore preferable that the reference electrode 2 is porous. Since the reference electrode 2 is also a field of electric and chemical reaction for ionizing $O_2$ contained in the reference gas, the material therefor is platinum (Pt) have a capability of adsorbing $O_2$ and in ionizing it. Also, it is possible to use an alloy having mainly Pt with palladium (Pd) or rhodium (Rh) or the like or a cermet material composed of Pt, Pt alloy and a solid electrolyte material. Incidentally, the reason why the cermet is used as a material of the reference electrode 2 is that a large reaction field should be provided since the electric chemical reaction for ionizing oxygen contained in the reference gas occurs in a contact interface amoung gas phase, the metal electrode and the solid electrolyte, and that the peeling or the like of the electrode by a thermal stress in use at a high temperature is prevented by balancing the enhancement in the contactability between the electrode and the solid electrolyte and the thermal expansion coefficients.

As the mounting method of the reference electrode 2 to the solid electrolyte plate 1, the methods mentioned below are simplest and easiest: a paste including Pt or a paste composed of cermet of Pt and a solid electrolyte is printed on the surface of the solid electrolyte plate 1 by a screen printing method or the like, a platinum mesh is pressed thereto in a condition that the paste is not dried, and then the resultant is dried and baked. Alternatively, a Pt mesh is dipped in slurry including Pt thus treated Pt mesh is mounted on a solid electrolyte plate 1, under a condition that the slurry is not dried, and the resultant is baked. Indeed, it is possible to use the paste as the electrode as it is after the paste is screen-printed. The baking step can be performed simultaneously with the baking of the sensing electrode 3 formed on the opposite surface of the solid electrolyte plate 1 to the reference electrode 2, or can be performed in order separately. With respect to the mounting of the Pt lead line 4 to the reference electrode 2, in the case where the reference electrode 2 is a Pt mesh, it is preferred to weld the Pt lead line 4 and the Pt mesh in advance by means of an arc weld or a spot weld since the mounting strength is high. Also, in the case of the formation of the electrode only by a screen printing, it is possible to mount the Pt lead line 4 by baking. A Pt plating method or platinum chloride film baking method can be illustrated as other methods.

On the other hand, the sensing electrode 3 is formed on the surface of the solid electrolyte plate 1 opposite the surface on which the reference electrode 2 is mounted. In the same manner as the case of the reference electrode 2, the sensing electrode 3 is electrically connected to the solid electrolyte plate 1. Also, since the function for producing and separating carbon dioxide by oxidization of the CO gas adsorbed to the metal component contained in the electrode and the oxygen ion moving through the solid electrolyte in the contact interface among the gas phase, the metal electrode, and the solid electrolyte is required for the sensing electrode 3, it is preferable that the sensing electrode 3 is porous. Also, the material that is suitable for this is the material having characteristics that would not accelerate the oxidization of CO gas by coexisting oxygen. Namely, it is preferable that oxygen ion ($O_{2-}$) that has moved through the solid electrolyte from the side of the reference electrode is reacted with CO gas to produce an electron ($e_-$) as shown in the following equation(II) without the reaction between the adsorbed oxygen (O(ad)) and CO gas as shown in the following equation(I). The thus produced electron is applied to the CO gas measurement.

$$CO+O(ad) \rightarrow CO_2 \tag{I}$$

$$CO+O^{2-} \rightarrow CO_2+2e^- \tag{II}$$

For this reason, in the present invention, Au is preferably used. It is preferable to use an Au alloy obtained by adding other noble metal of 0.1 to 10 wt % to Au as a sensing electrode. Another noble metal of 1 to 10 wt %, preferably, 0.1 to 5 wt %, more preferably, 0.1 to 1 wt % is added to Au to thereby suppress the coagulation of Au particles at a high temperature during the manufacture of the sensing electrode and to make it possible to maintain the porosity of the sensing electrode and to enlarge the surface area of the sensing electrode. As a result, it is possible to more enhance the detecting sensitivity. Incidentally, the metal to be made an alloy with Au is Rh, Pt, Pd, silver (Ag) or the like. In this case, the content of Au is 90 wt % or more, preferably, 95 wt %, more preferably, 99 wt %. The content of Au can be suitably selected in view of the melting point of an alloy, the baking temperature or the operation temperature of the sensor. The preparation method for an alloy in question is well known in the art.

Of course, it is possible to suitably use a cermet electrode obtained by mixing the same material as that of the solid electrolyte plate to Au or above-described Au alloy. The reason for using the cermet material is the same as in the case of the reference electrode 2.

Figure 16:
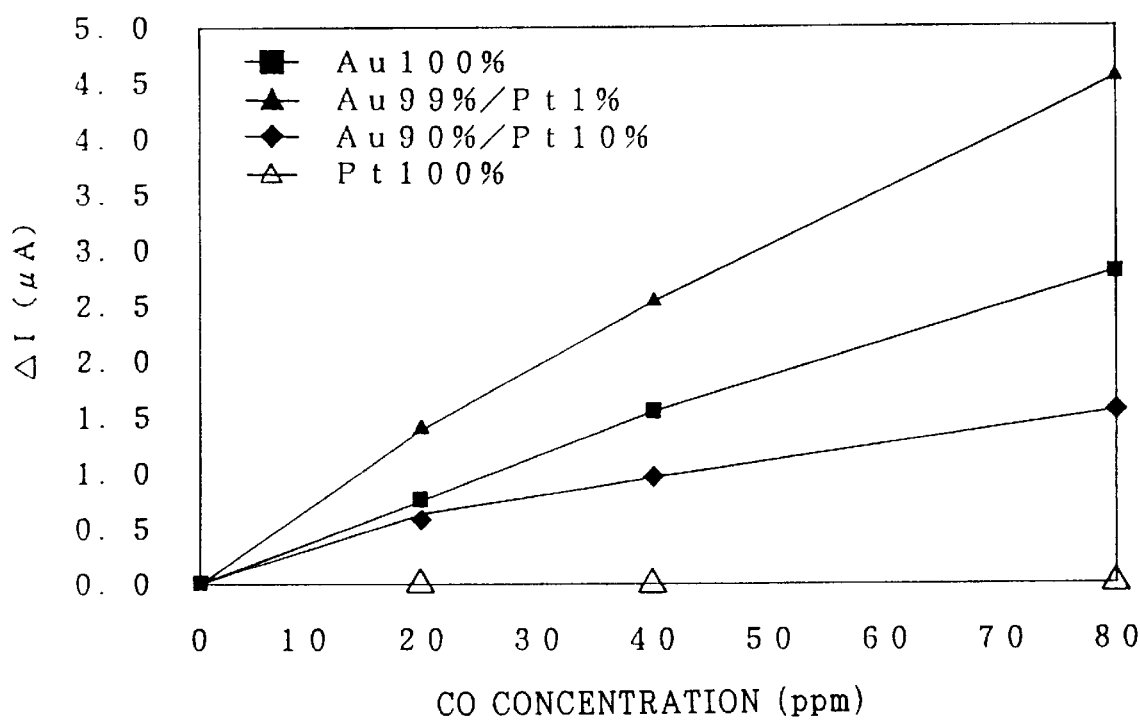
FIG. 16 is a graph showing the measurement result on the affect of the Au alloy formation to the CO gas measurement sensitivity.

A comparison test of the detecting sensitivity to the CO gas concentration was conducted by using Au 100 wt %, and two kinds of Au 90 wt % alloy with Pt and Au 99 wt % alloy with Pt as the CO sensing electrode, and by using the gases, to be measured, containing the CO gas concentration of 0, 20, 40 and 80 ppm respectively. As a result, as shown in FIG. 16, the sensing electrode using the alloy of Pt 1 wt % and Au 99 wt % exhibits the highest sensitivity. Also, as the CO concentration is increased, the alloy shows a more excellent detecting sensitivity than that of the Au 100 wt %. Among the alloys, the alloy of Au 99 wt % and Pt 1 wt % exhibits a more excellent detecting sensitivity.

The sensing electrode of Pt 100 wt % was used as a comparison CO sensing electrode. However, the sensitivity thereof for the sensing electrode for the CO gas concentration was low and the change of the detecting sensitivity due to the CO gas concentration is not acknowledged.

The mounting process of the sensing electrode 3 onto the solid electrolyte plate 1 and the mounting process of the sensing electrode 3 to the lead line 5 are performed in the same manner as in the case for the above-described reference electrode 2. As an electrode material, it is possible to use a paste containing Au, an Au alloy or a mixture of one or more of the above-described noble metals and Au, or a paste composed of a cermet between a solid electrolyte and Au, Au mesh or an Au alloy mesh, and Au lead line 5. Also, as another method of forming the sensing electrode, it is possible to apply Au plating, sputtering or the like.

In the case where the fine particle layer is formed by using fine particles of Au or Au alloy and electrode film is formed thereon to form a sensing electrode, a paste in which fine particles are diffused is applied on the solid electrolyte, and the resultant is baked. Alternatively, a fine particle layer and an electrode film are coated in order, and thus coated layer and film are baked simultaneously.

Incidentally, fine particles of Au and an Au alloy means the particles having an average size of 0.01 to 10 $\mu$, preferably, 0.01 to 1 $\mu$, more preferably, 0.01 to 0.1 $\mu$. The shape of the particles is not always spherical, but can be granular, a rugby ball like form or the like.

The solid electrolyte plate 1 on which the electrodes are mounted is inserted into the base 6. The solid electrolyte plate 1 serves as the partition for partitioning the reference gas atmosphere and the measurement gas atmosphere. The glass melting material or the like can be used as the seal between the solid electrolyte plate 1 and the base 6. Also, air is usually used as the reference gas. In the case where such a partition wall type structure is taken, the electromotive force caused by the difference between the respective CO gas partial pressures of the reference gas and the measurement gas is measured to thereby determine the CO gas concentration contained in a gas to be measured. In this case, there is no problem even if the reference electrode 2 and the sensing electrode 3 are made of the same material.

Figure 2:
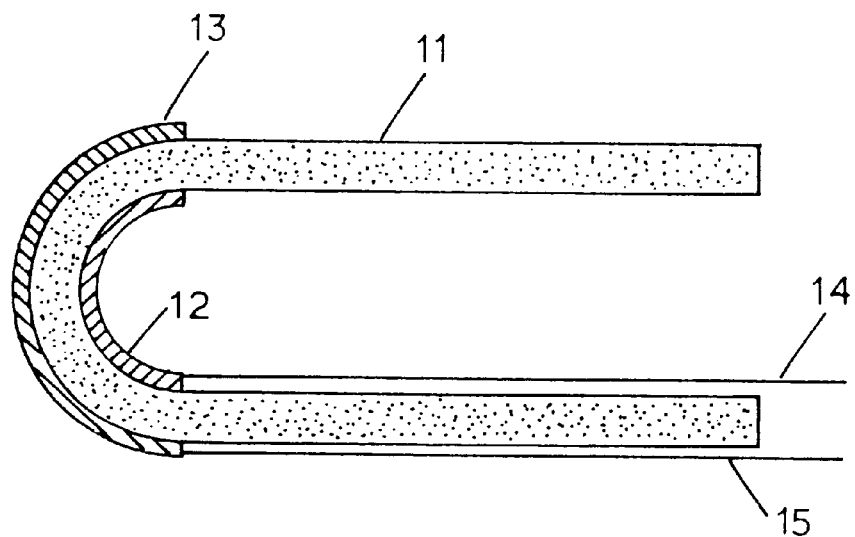
FIG. 2 is a cross-sectional view showing a CO gas sensor according to an embodiment of the present invention.

FIG. 2 shows another embodiment of the present invention. A reference electrode 12 is formed inside of the tip end portion of the solid electrolyte base 11 having a bottomed cylindrical shape. A sensing electrode 13 is formed on the outside. A Pt lead line 14 and an Au lead line 15 are drawn from the respective electrodes. The solid electrolyte base 11 having the bottomed cylindrical shape can readily be produced by baking a molded article by a casting molding, an extruding molding, an injection molding or the like. In mounting the respective electrodes, the same way as in the first embodiment shown in FIG. 1 can be utilized; that is, a paste containing an electrode material or the like is coated to a position where the electrode is to be mounted, then thus coated paste is baked with pressing the mesh of the electrode thereto. Since this embodiment also takes a structure for separating the measurement gas and the reference gas, the sensor forms a rich/lean cell. Accordingly, it is possible to form the reference electrode 12 of the same material as Au or an Au alloy of the sensing electrode 13.

Figure 3:
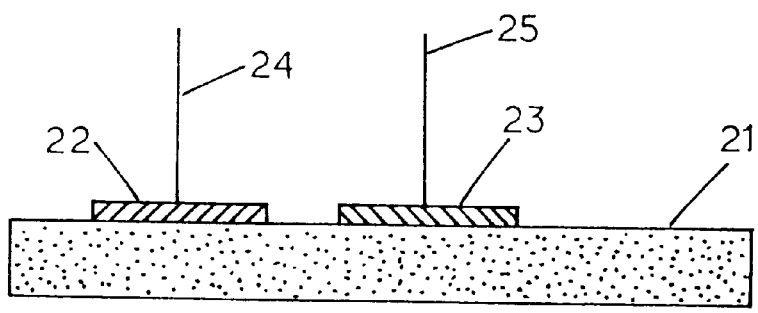
FIG. 3 is a cross-sectional view showing a CO gas sensor according to another embodiment of the present invention.

On the other hand, FIG. 3 shows further another embodiment of the present invention. A reference electrode 22 and a sensing electrode 23 are mounted on the same surface of a solid electrolyte plate 21. A Pt lead line 24 and an Au lead line 25 are mounted on the respective electrodes. In this case, it is unnecessary to use the reference gas. The sensor element as a whole is provided in the measurement gas atmosphere. Also, the shape of the solid electrolyte plate 21 is not limited to a plate-like shape but can be cylindrical, like a rod or the like. There is no special limit to the shape.

In this embodiment, it is preferable that the material of the reference electrode 22 is different from that of the sensing electrode 23. This is because the electromotive force generated due to the difference in electrode reaction between the CO gas sensing electrode 23 and the reference electrode to thereby make it possible to measure the CO gas concentration in the gas to be measured.

Figure 4:
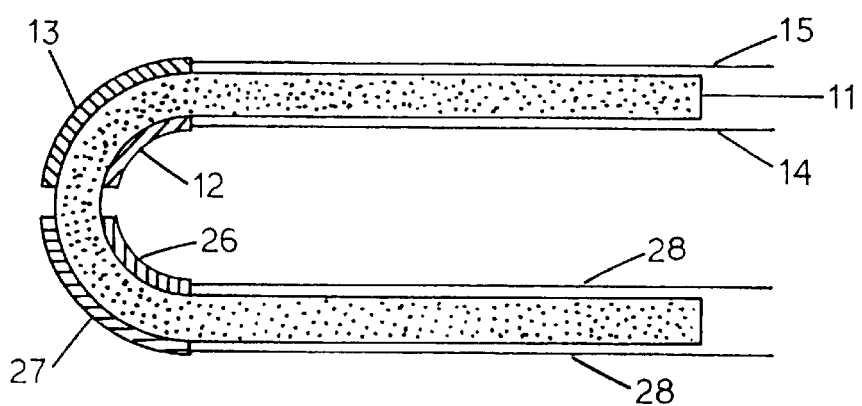
FIG. 4 is a cross-sectional view showing a CO gas sensor according to an embodiment in which oxygen measurement electrodes are formed.

FIG. 4 shows another embodiment in which an electrode for measuring oxygen is mounted on the structure shown in FIG. 2 to measure simultaneously the CO gas concentration and $O_2$ concentration. By using the measurement result of the oxygen gas concentration, the effect due to the reaction of oxygen contained in the measurement result of CO gas is excluded and compensated for. Thus, it is possible to measure the CO gas concentration with higher precision. In this embodiment, it is possible to use the same electrode 12 and sensing electrode 13 for measurement of the CO gas as those of the embodiment shown in FIG. 2. Then, reference electrode 26 and sensing electrode 27 for the measurement of oxygen are basically an oxygen sensor. Accordingly, it is preferable to use porous Pt electrodes which are used as the electrodes of the conventional zirconia oxygen sensor. Also, a mounting method of the lead line 28 and the mounting method of these electrodes for the oxygen measurement can be carried out in the same way as in the case of the CO gas measurement electrodes. A Pt line is preferably used as the lead line 28. Also, it is understood that this embodiment can readily be applied to a planar element shown in FIG. 1. Also, the reference electrode may be commonly used for the measurement of CO gas and oxygen gas.

Figure 5:
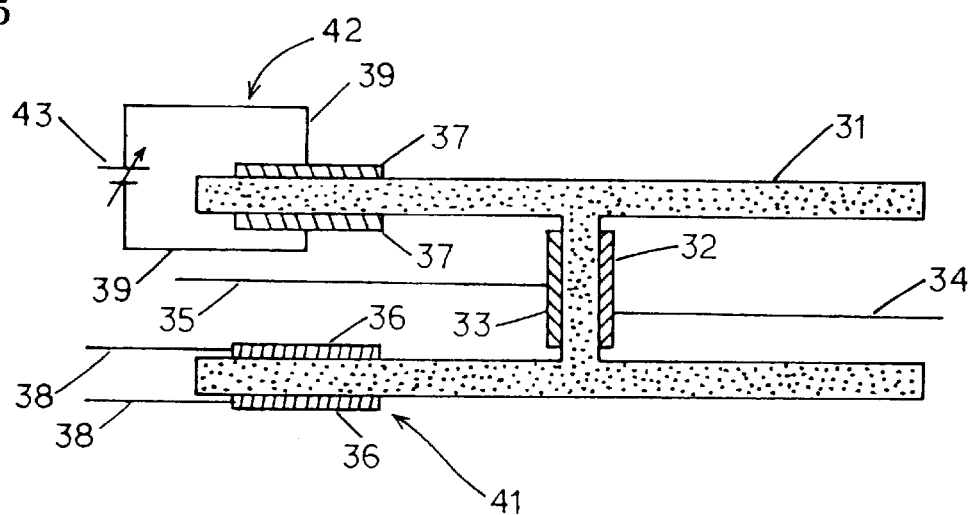
FIG. 5 is a cross-sectional view showing a CO gas sensor according to an embodiment in which an oxygen pump is provided.

Furthermore, FIG. 5 shows an embodiment of a sensor in which a solid electrolyte base 31 having an H-shaped and two recess portions is used. One of the recess portions is brought into contact with the reference gas atmosphere. A reference electrode 32 made of porous Pt is mounted on the bottom portion of the recess portion. A Pt lead line 34 is mounted on the reference electrode 32. The other recess portion is brought into contact with the measurement gas atmosphere. A sensing electrode 33 made of Au or an Au alloy is provided on a bottom portion of the recess portion. An Au lead line 35 is mounted on the sensing electrode 33. Furthermore, an oxygen pump cell 42 and an oxygen measurement sensor 41 are mounted on side walls of the recess portion. In this case, each one of the electrodes 36 of the oxygen measurement sensor 41 and the electrodes 37 of the oxygen pump cell 42 are formed inside of the recess portion, whereas the other electrodes are formed outside of the recess portion. All the electrodes are brought into contact with the measurement gas atmosphere. In this case, it is preferable that the electrodes 37 of the oxygen pump cell have the characteristics not to oxidize CO gas. It is preferable to use conductive metal oxide electrode such as lanthanum manganite ($LaMnO_3$) or the like therefor.

Pt lines are suitably used for both the lead lines 38 and 39 mounted on the electrodes 36 and 37 respectively. Since the electrodes 37 are a ceramic electrode, it is impossible to mount the lead line 39 directly to the electrode. The surface of the electrode is metallized first and the lead line 39 is baked thereto. This method is usually used.

With such a structure, the oxygen pump cell is driven by controlling a potentiostat 43 so as to keep the oxygen concentration in the measurement gas atmosphere at a constant level by the oxygen measurement sensor. Accordingly, since the oxygen concentration by the CO gas sensing electrode of the measurement gas is always kept constant, it is possible to measure CO gas while easily excluding the adverse affect of oxygen generated in the sensing electrode 33 for measuring CO gas. It is thus possible to further enhance the measurement precision.

Figure 6:
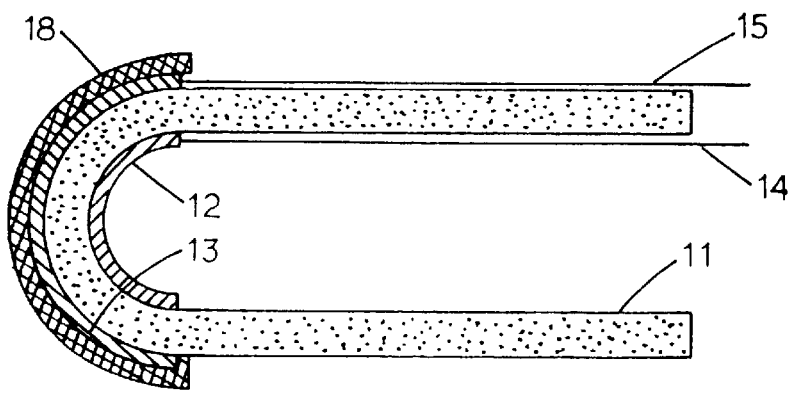
FIG. 6 is a cross-sectional view showing a CO gas sensor according to the present invention in which a gas diffusion regulating layer is formed.

FIG. 6 shows an embodiment in which a gas diffusion regulating layer 18 is mounted on a surface of the CO measurement sensing electrode 13 in the embodiment shown in FIG. 2. The gas diffusion regulating layer 18 is a gas diffusion regulating layer for suppressing the diffusion contact of a flammable gas other than CO gas, for example, a flammable gas having high molecular weight such as hydrocarbon, such as propane or butane to the surface of the sensing electrode 13. By providing such a gas diffusion regulating layer 18, it is possible to enhance the selectivity of CO gas in the sensor according to the present invention. More specifically, a zeolite film or the like is used. In a method of producing this, the material is laminated and formed on the surface of the sensing electrode 13 by a method such as dipping, or it is possible to form the layer by a method such as sputtering or screen printing after the sensing electrode 13 has been formed on the solid electrolyte base 11. Also, needless to say, such a gas diffusion regulating layer 18 can be applied to any one of the foregoing embodiments.

By the way, with respect to the measurement method for the CO gas concentration in the thus far described CO gas sensor according to the present invention, first of all, in a structure for separating the reference gas atmosphere and the measurement gas atmosphere by using the electrolyte plate as the partitioning wall, the rich/lean cell is formed so that the CO gas concentration may be measured from the electromotive force of the rich/lean cell. Also, in the case where the overall structure of the sensing electrode and the reference electrode formed on the solid electrolyte is disposed in the measurement gas atmosphere, the material of the sensing electrode and the material of the reference electrode for the CO gas measurement are differentiated from each other to thereby measure the electromotive force generated between the respective electrodes to know the CO concentration.

In addition, according to the present invention, in all the above-described embodiments, a constant current is caused to flow between the sensing electrode and the reference electrode for the CO gas measurement. In this case, the electromotive force change caused by the adsorption and oxidization of CO gas by the sensing electrode is measured so that the CO gas concentration can be measured. According to this method, the oxidizing reaction of CO gas on the electrode is accelerated so that the sensitivity of the sensor to the CO gas can be enhanced. Also, the current between the sensing electrode and the reference electrode which is required to keep the voltage constant between the sensing electrode and the reference electrode for the CO gas measurement is measured to ensure the same effect as the above-mentioned.

Figure 7:
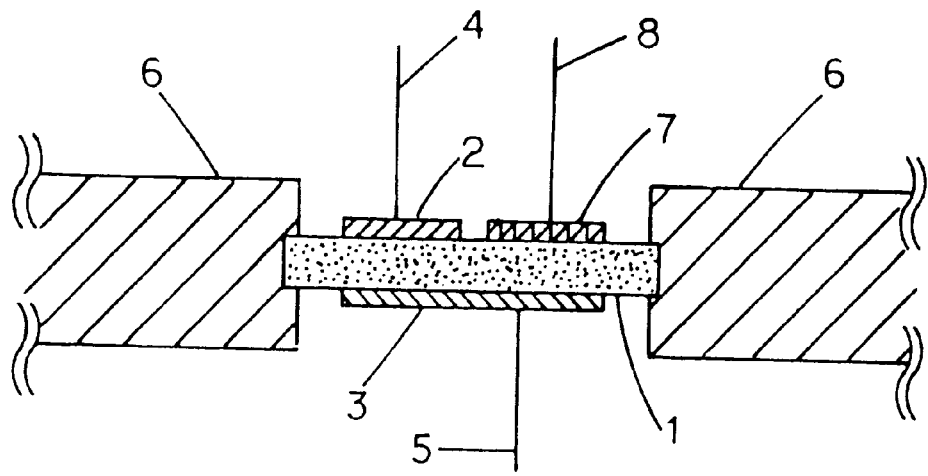
FIG. 7 is a cross-sectional view showing a CO gas sensor according to the present invention in which an auxiliary reference electrode is formed.

Furthermore, FIG. 7 shows a structure in which an auxiliary CO gas measurement reference electrode 7 is formed in the basic structure for the present CO gas sensor shown in FIG. 1. This auxiliary reference electrode 7 is made of porous Pt in the same manner as in the case of the reference electrode 2. A Pt line is used as a lead line 8. In the CO gas sensor having this structure, a voltage between the auxiliary reference electrode 7 and the sensing electrode 3 is measured by applying a constant current between the reference electrode 2 and the sensing electrode 3 so that only the reaction of CO gas by the sensing electrode 3 is separately measured to thereby attain a higher precision measurement.

Figure 8:
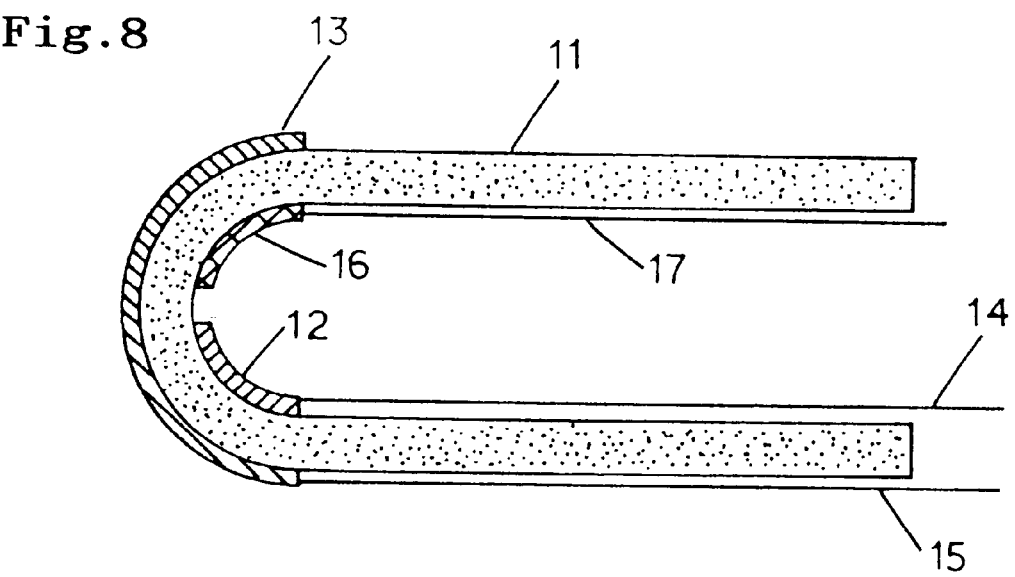
FIG. 8 is a cross-sectional view showing a CO gas sensor according to another embodiment in which an auxiliary reference electrode is formed.

FIG. 8 shows an embodiment in which an auxiliary reference electrode 16 on which a Pt lead line 17 is mounted is formed in the structure using the electrolyte base 11 having the bottomed cylindrical shape shown in FIG. 2. The function of the auxiliary reference electrode 16 is the same as that of the auxiliary reference electrode 7 shown in FIG. 7.

Figure 9:
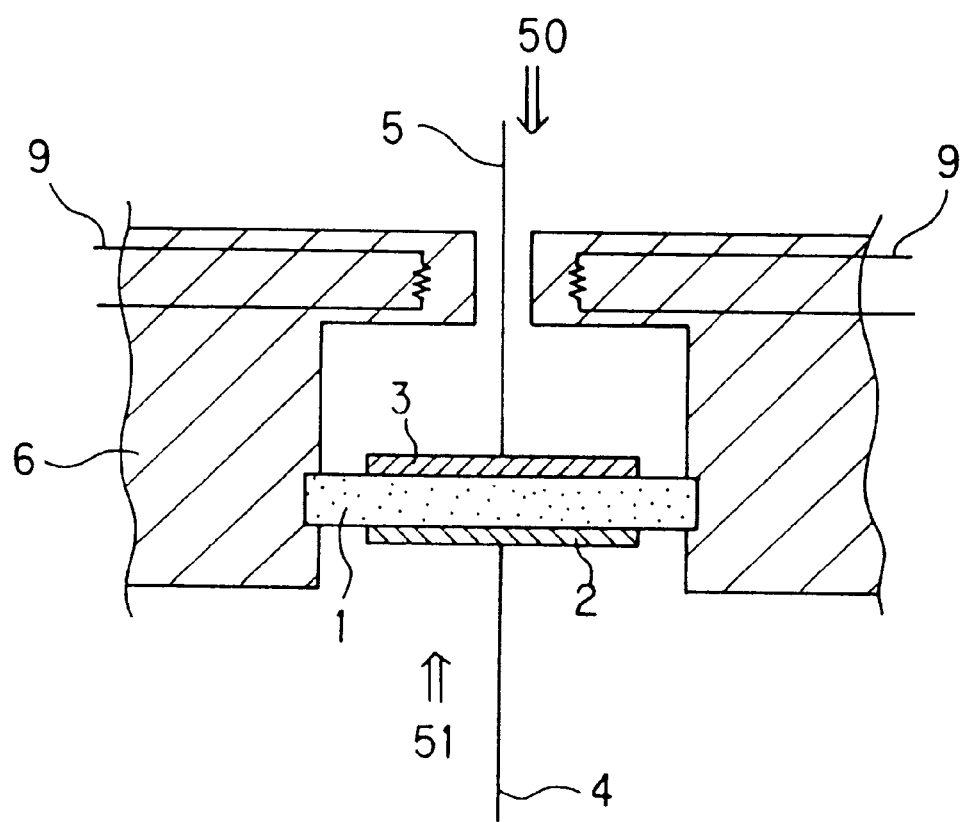
FIG. 9 is a cross-sectional view showing an embodiment in which a high temperature pre-treatment portion is provided in a part of the CO gas sensor shown in FIG. 1.

FIG. 9 is a cross-sectional view showing a basic structure in which a high temperature pre-treatment portion 9 is provided as a high temperature section to the base 6 on the side of the inlet of the gas to be measured upstream of the CO gas measurement sensing electrode 3 in the flow path of the measurement gas 50 of the CO gas sensor shown in FIG. 1. The measurement gas 50 is heated 850 to 950° C. before it reaches the CO gas sensing electrode by a heater provided in the high temperature pre-treatment portion 9, for example, at the vicinity of the measurement gas inlet of the base 6. The measurement gas 50 is heated in this portion at a temperature of 850 to 950° C. so that NOx or SOx contained in the measurement gas is caused to reach the chemical equilibrium at about sensor temperature and the interference with the CO gas measurement sensing electrode by the NOx or $SO_2$ is prevented or substantially eliminated. With such a structure, it is possible to attain the measurement of the CO gas concentration with higher precision.

Figure 17:
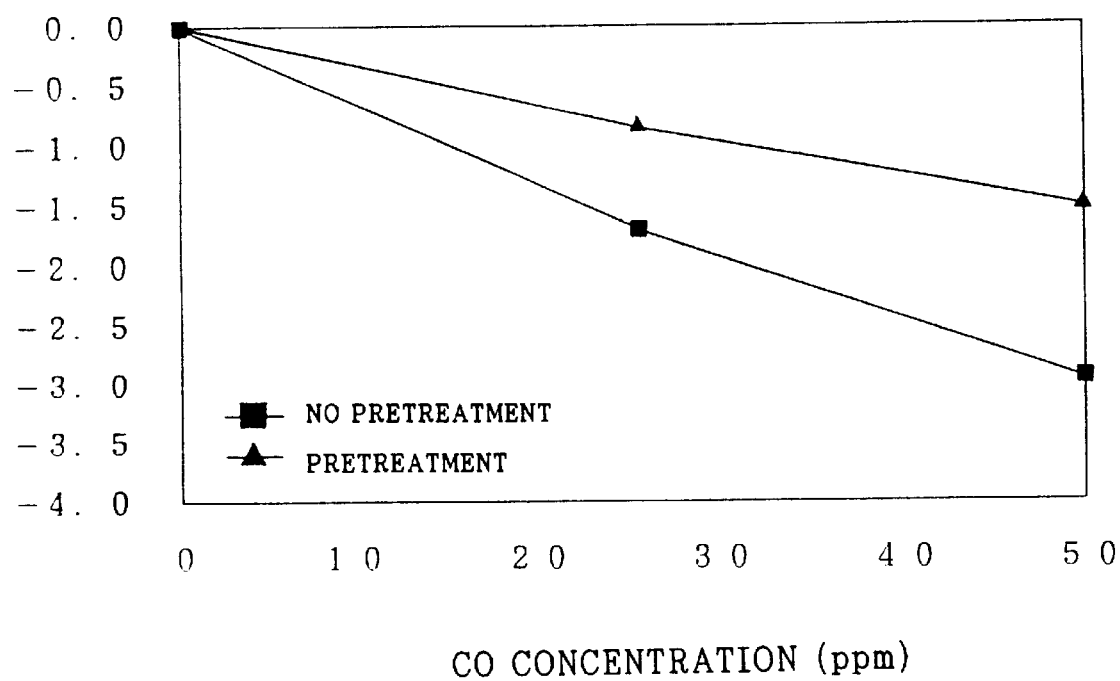
FIG. 17 is a graph showing the measurement result on the affect to the CO gas measurement sensitivity in the case where the measurement gas is heated by a high temperature pre-treatment portion.

The affect of the monoxide gas sensor electrode in accordance with the present invention to the detecting sensitivity was tested when the gas to be measured was heated at 850° at the high temperature pre-treatment portion 9 by using the sensor shown in FIG. 9. The affect to the detecting sensitivity of the sensor was measured when the high temperature pre-treatment portion 9 was heated by a heater by using the CO concentrations of 0, 10, 20, 30, 40 and 50 ppm in the gas to be measured. The total result is shown in FIG. 17. From this, it is understood that the CO gas detecting sensitivity is enhanced by the pre-treatment at the high temperature pre-treatment portion 9.

Figure 10:
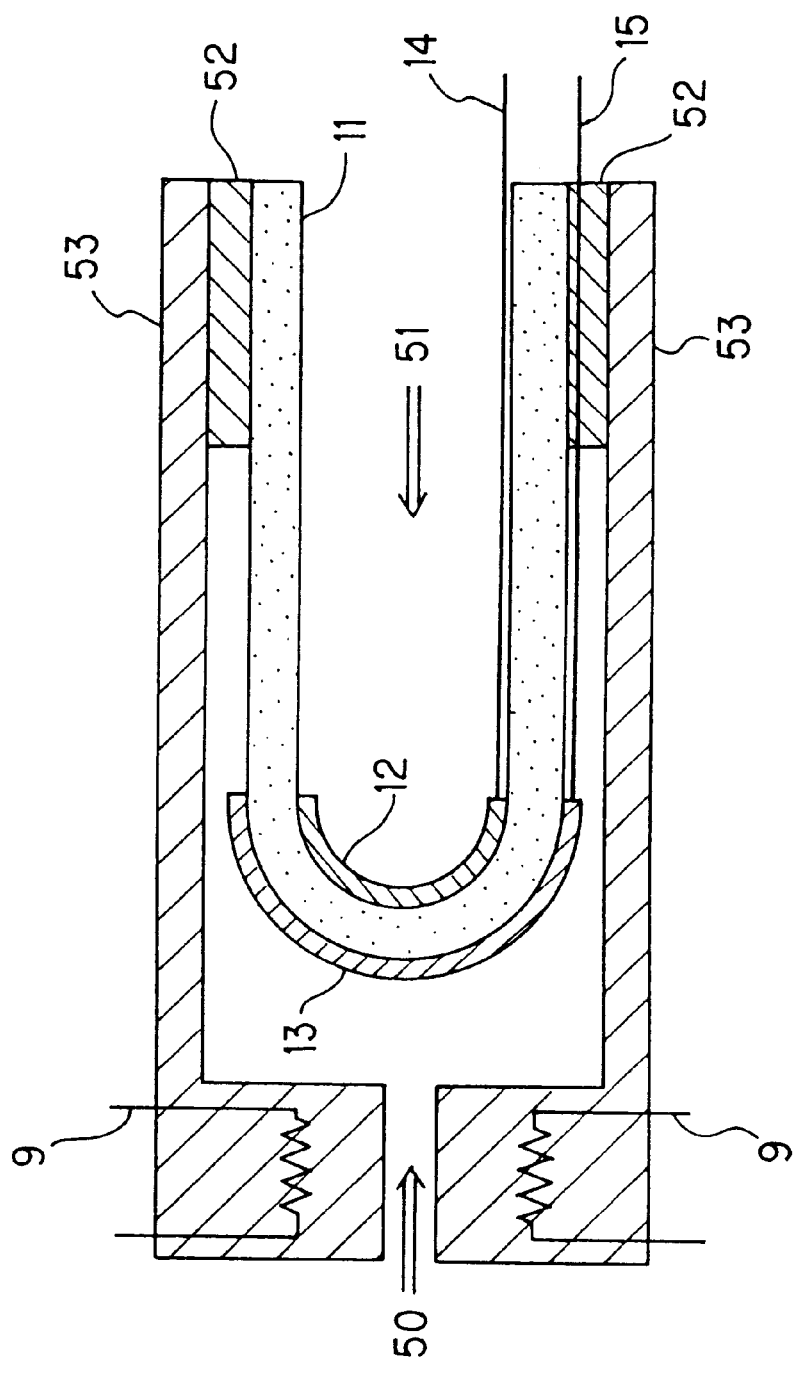
FIG. 10 is a cross-sectional view showing an embodiment in which a high temperature pre-treatment portion is provided in a part of the CO gas sensor shown in FIG. 2.

FIG. 10 shows a basic structure in which a high temperature pre-treatment portion 9 is provided as a high temperature pre-treatment section on the side of the inlet of the gas to be measured upstream of the CO gas measurement sensing electrode in the flow path of the measurement gas 50 of the CO gas sensor shown in FIG. 2. A sealant 52 is disposed between the solid electrolyte base 11 and the high temperature pre-treatment portion 9 so as to fix integratedly the CO gas measurement sensing electrode 13 and a support member 53 for the high temperature pre-treatment portion 9, such as a heater, and to prevent the measurement gas 50 from flowing to the outside of the sensor out of contact with the CO gas measurement sensing electrode 13. The material that would not affect the detection of the CO gas may be selected and used as the support member 53 for the high temperature pre-treatment portion.

Also, with the sealant, there is no limit other than the non-reactivity with the CO gas. It is preferable to use as a sealant ceramic such as alumina or zirconia. In the same way as in the sensor shown in FIG. 9, it is possible to exactly measure the CO gas concentration.

Figure 11:
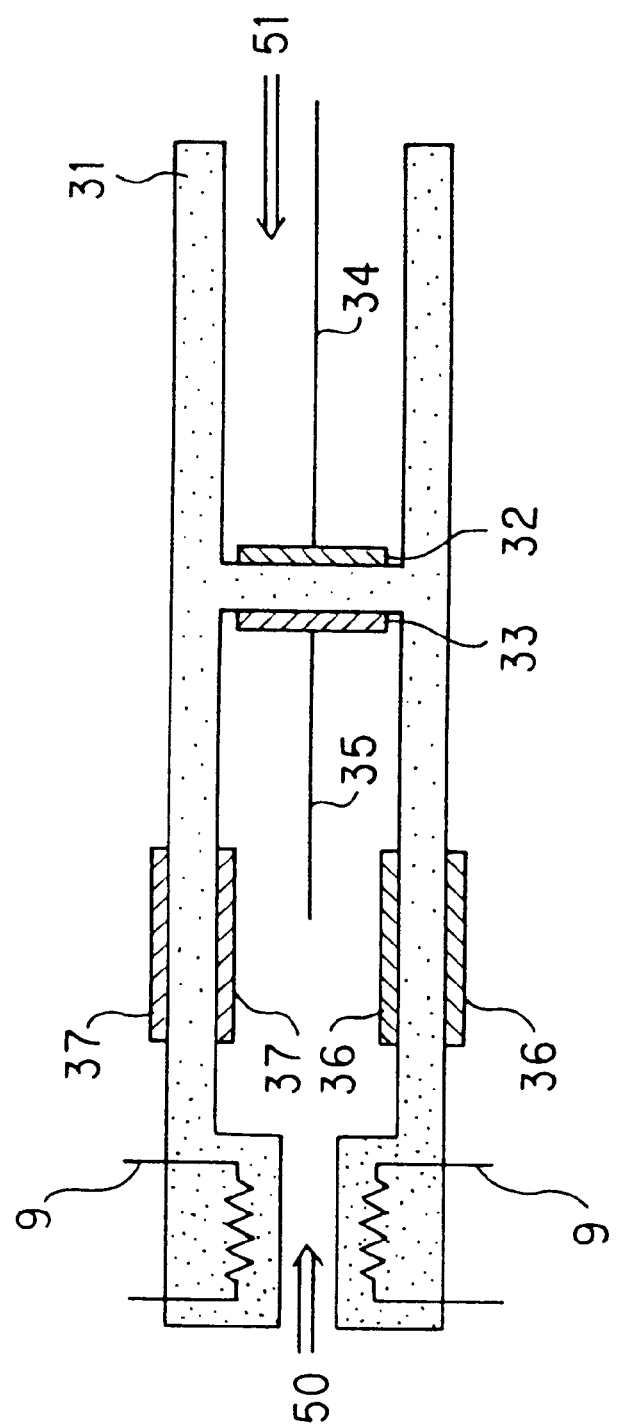
FIG. 11 is a cross-sectional view showing an embodiment in which a high temperature pre-treatment portion is provided in a part of the CO gas sensor shown in FIG. 5.

FIG. 11 shows a basic structure in which a heater is provided in a part of the solid electrolyte base 31 as a high temperature pre-treatment portion 9 upstream of an oxygen measurement electrode 36 and oxygen pump cell electrode 37 in the flow path of the measurement gas 50 of the CO gas sensor shown in FIG. 5. Incidentally, FIG. 11 the pump cell electrode is depicted, however, the oxygen pump 42 and the potentiostat 43 are not depicted therein.

In the case shown in FIG. 11, it is possible to more exactly measure the CO gas concentration in the same manner as in the sensor shown in FIG. 9.

Figure 18:
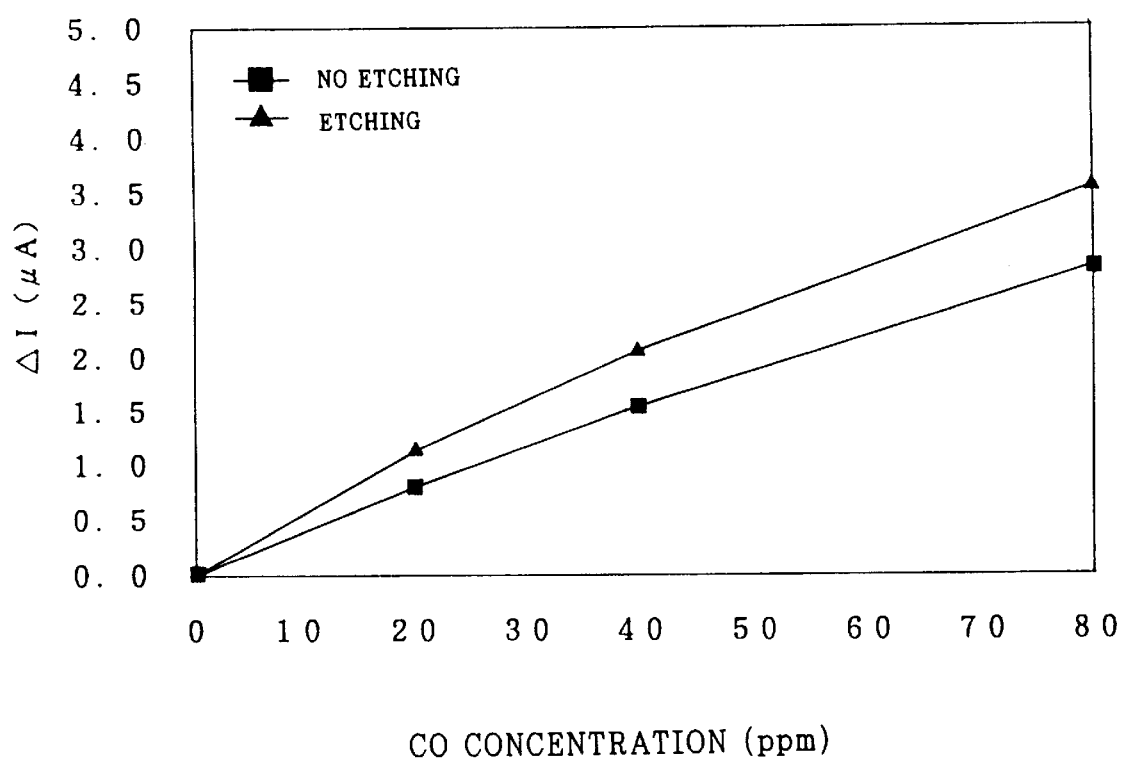
FIG. 18 is a graph showing the measurement result of the affect to the CO gas measurement sensitivity in the case where the sensing electrode is used, in which the surface of the solid electrolyte in contact with the sensing electrode is chemically etched.

FIG. 12 is a cross-sectional view showing a condition of jointing portion between the electrolyte and the CO gas sensing electrode in the case where the CO gas electrode is formed on the roughed surface of the electrolyte to be contact with the sensing electrode after having been roughened by chemically etching said surface. Thus, the area of the contact interface among the gas phase, the metal electrode and the solid electrolyte is thus increased so that the detecting sensitivity of the CO gas concentration can be enhanced. The CO gas detecting sensitivity when the CO gas sensing electrode which was formed by roughing the surface by etching was tested in comparison with the case where the CO gas electrode was formed without any chemical etching. The detecting sensitivity of the two electrodes was measured by using the measurement gas containing the CO gas of 0, 20, 40 and 80 ppm. The result is shown in FIG. 18. As is apparent from the result of FIG. 18, it is apparent that the detecting sensitivity is enhanced by increasing the area of the contact interface of the above-mentioned three by etching.

Also, the detecting sensitivity of the CO gas is enhanced also in the case the fine particle layer of Au or Au alloy is formed between the solid electrolyte and the electrode instead of the chemical etching.

Figure 13:
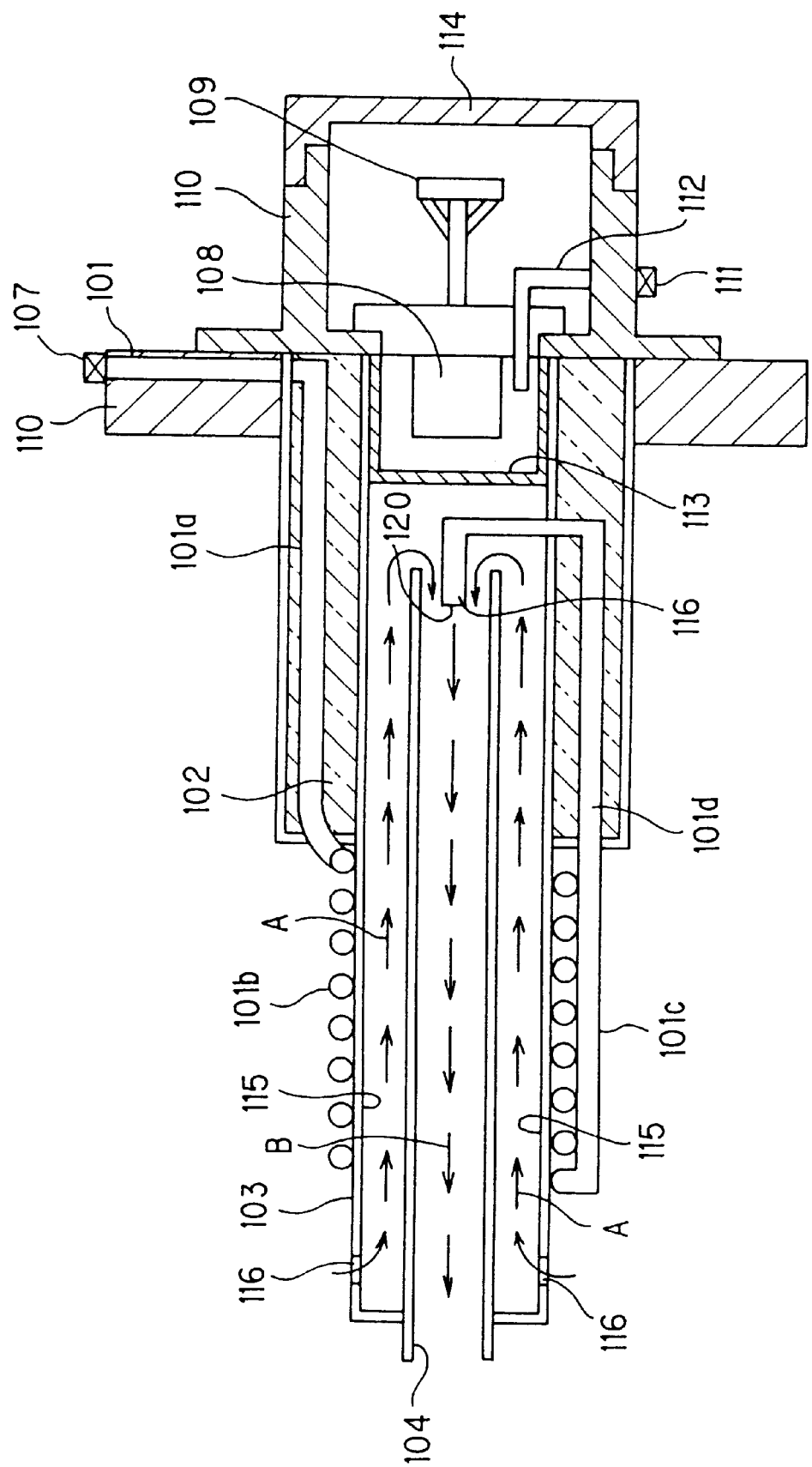
FIG. 13 is a cross-sectional view showing a CO gas measuring device on which the CO gas sensor according to the present invention is mounted.

FIG. 13 is a schematic view of a basic structure of a direct coupling type CO gas measurement apparatus having the CO gas sensor shown in FIG. 1. The structure includes a sensor case 110 having a sensor device mounting portion 118, a sensor cover 114 detachably mounted on the sensor case 110, a CO gas sensor 108 received in the sensor box according to the present invention, a fastening base 109 for fastening the sensor 108, a reference gas feed pipe 112, a filter 113 made of porous ceramics and provided in front of the sensor 108, a measurement gas sampling tube 103 having a double structure and an ejector gas feed pipe 101.

The measurement gas sampling tube 103 is formed into the double structure in which a measurement gas sampling path 115 is formed on the outer side and a measurement gas discharge path 104 is formed on the inner side.

An ejector gas feed port 107 is provided at one end of the ejector gas feed pipe 101. The ejector gas feed pipe 101 passes through a heat insulator 102 as shown by 101a; thereafter, reaches an exposed ejector gas feed pipe portion 101b having a spiral shape wound around the outer periphery of the measurement gas sampling tube 103 in an exposed condition; subsequently, is connected to the exposed linear ejector gas feed pipe portion 101c; again passes through the heat insulator 102 as shown by 101d; is exposed in the interior of the measurement gas sampling tube 103; and is connected to the ejector 106.

When the ejector gas is fed from the ejector gas feed port 107, the ejector gas passes through the embedded portion 101a in the heat insulator 102, the exposed portion 101b, the exposed portion 101c and the embedded portion 101d in the heat insulator 102 in this order and is blown out of the ejector blow port 120. Thus, a vacuum pressure is generated around the ejector 106 to form a convection flow. As a result, the measurement gas from the outside of this device is sampled by the sampling port 116 and is caused to flow through the measurement gas sampling path 115 as indicated by arrows A and to be reversed in the measurement gas discharge path 104 as indicated by arrows B to be discharged again to the outside of the device. In the meantime, the CO gas contained in the measurement gas is measured by the sensor 108.

Figure 14:
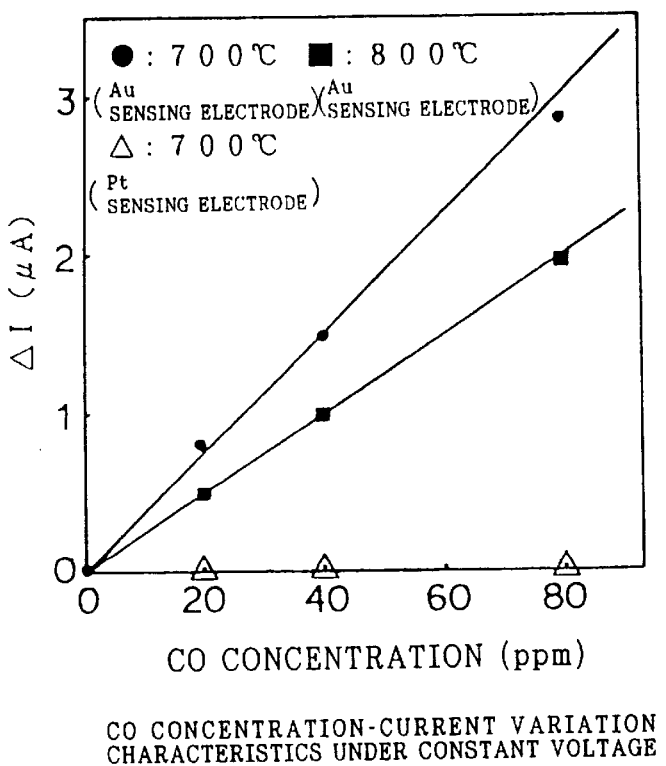
FIG. 14 is a graph showing a CO gas measurement result in the case where the CO gas sensor according to the present invention is used.
Figure 15:
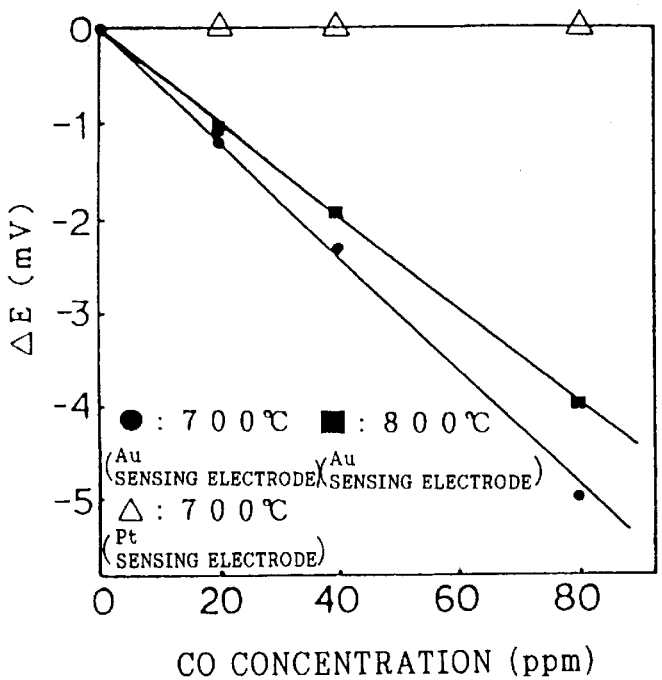
FIG. 15 is another graph showing a CO gas measurement result in the case where the CO gas sensor according to the present invention is used.

FIGS. 14 and 15 show one example of results obtained by the measurement of the CO gas concentration by using the sensor according to the present invention. Incidentally, in this case, the measurement result obtained by using Pt as a sensing electrode is also shown in FIGS. 14 and 15 for comparison. As is apparent from these graphs, the sensitivity to CO gas is in proportion to the CO gas concentration. Also, it is understood that in the case where the oxygen concentration in the measurement gas is varied, there is no adverse affect to the CO gas measurement due to the oxygen sensor and the drive of the oxygen pump. Incidentally, it is possible to measure the concentration at a constant temperature of a high temperature gas if such a structure is taken in which, in order to reduce the temperature dependency of the electromotive force difference caused by the reaction of the CO gas, a temperature measurement element and a heater are provided close to or integrally with the solid electrolyte so that the solid electrolyte can be heated and maintained at a temperature of 600 to 900° C.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. A carbon monoxide gas sensor comprising:

a solid electrolyte having an oxygen ion transfer property;

carbon monoxide gas measurement sensing and reference electrodes electrically connected to at least part of the surface of the solid electrolyte;

an auxiliary reference electrode for carbon monoxide gas measurement; and oxygen measurement sensing and reference electrodes;

wherein gold or a gold alloy is used in the carbon monoxide gas measurement sensing electrode.

2. The carbon monoxide gas sensor according to claim 1, further comprising means to cause a constant current to flow between the carbon monoxide gas measurement sensing electrode and the reference electrode and means to measure an electromotive force change, between the carbon monoxide gas measurement sensing electrode and the auxiliary reference electrode, caused by the absorption/oxidation of carbon monoxide in the sensing electrode when a constant current is cause to flow between the carbon monoxide gas measurement sensing and reference electrodes, to thereby determine the concentration of carbon monoxide gas.

3. The carbon monoxide gas sensor according to claim 1, further comprising means to maintain a constant voltage between the carbon monoxide gas measurement sensing electrode and the reference electrode and means to measure a current value, between the carbon monoxide gas measurement sensing electrode and the auxiliary reference electrode, cause by the oxidation of carbon monoxide gas in the sensing electrode when a constant voltage is maintained between the carbon monoxide gas measurement sensing and reference electrodes, to thereby determine the concentration of carbon monoxide gas.

4. A carbon monoxide gas sensor comprising:

a solid electrolyte having an oxygen ion transfer property;

carbon monoxide gas measurement sensing and reference electrodes electrically connected to at least part of the surface of the solid electrolyte; and oxygen measurement sensing and reference electrodes;

wherein gold or a gold alloy is used in the carbon monoxide gas measurement sensing electrode;

wherein the solid electrolyte comprises zirconium oxide and a stabilizer which comprises one or more selected from the group consisting of magnesium oxide, calcium oxide, yttrium oxide, cerium oxide, scandium oxide, and rare earth metal oxides; and wherein the electrodes other than the carbon monoxide gas measurement sensing electrode are cermet electrodes comprising a mixture of porous platinum or platinum and the same material as that of the solid electrolyte.

5. A carbon monoxide gas sensor comprising:

a solid electrolyte having an oxygen ion transfer property;

carbon monoxide gas measurement sensing and reference electrodes electrically connected to at least part of the surface of the solid electrolyte;

an auxiliary reference electrode for carbon monoxide gas measurement;

oxygen measurement sensing and reference electrodes; and an oxygen pump cell for controlling an oxygen concentration in a measurement atmosphere;

wherein gold or a gold alloy is used in the carbon monoxide gas measurement sensing electrodes.

6. The carbon monoxide gas sensor according to claim 5, further comprising means to cause a constant current to flow between the carbon monoxide gas measurement sensing electrode and the reference electrode and means to measure an electromotive force change, between the carbon monoxide gas measurement sensing electrode and the auxiliary reference electrode, caused by the adsorption/oxidization of carbon monoxide in the carbon monoxide gas measurement sensing electrode when a constant current is caused to flow between the carbon monoxide gas measurement sensing and reference electrodes, to thereby determine the concentration of carbon monoxide gas.

7. The carbon monoxide gas sensor according to claim 5, further comprising means to maintain a constant voltage between the carbon monoxide gas measurement sensing electrode and the reference electrode and means to measure a current value, between the carbon monoxide gas measurement sensing electrode and the auxiliary reference electrode, caused by the oxidization of carbon monoxide gas in the carbon monoxide gas measurement sensing electrode when a constant voltage is maintained between the carbon monoxide gas measurement sensing and reference electrodes, to thereby determine the concentration of carbon monoxide gas.

8. A carbon monoxide gas sensor comprising:
a solid electrolyte having an oxygen ion transfer property;
carbon monoxide gas measurement sensing and reference electrodes electrically connected to at least part of the surface of the solid electrolyte;
oxygen measurement sensing and reference electrodes; and
an oxygen pump cell for controlling an oxygen concentration in a measurement atmosphere;
wherein gold or a gold alloy is used in the carbon monoxide gas measurement sensing electrodes;
wherein the solid electrolyte comprises zirconium oxide and a stabilizer which comprises one or more selected from the group consisting of magnesium oxide, calcium oxide, yttrium oxide, cerium oxide, scandium oxide, and rare earth metal oxides; and
wherein the electrodes other than the carbon monoxide gas measurement sensing electrode are cermet electrodes comprising a mixture of porous platinum or platinum and the same material as that of the solid electrolyte.

9. A carbon monoxide gas sensor comprising:
a solid electrolyte having an oxygen ion transfer property;
carbon monoxide gas measurement sensing and reference electrodes electrically connected to at least part of the surface of the solid electrolyte;
said carbon monoxide gas measurement sensing electrode either (a) is formed by laying an electrode film on an Au or an Au alloy fine particle layer which is disposed on the solid electrolyte or (b) is a cermet electrode comprising gold or a gold alloy and the same material as that of the solid electrolyte;
oxygen measurement sensing and reference electrodes;
said carbon monoxide gas measurement sensing electrode and said reference electrode forming a pair of electrodes; said carbon monoxide gas measurement sensing electrode and said reference electrode being installed facing each other through the solid electrolyte or said carbon monoxide gas measurement sensing electrode and said reference electrode being aligned on same surface of the solid electrolyte;
means to simultaneously measure the carbon monoxide concentration and the oxygen concentration; and
means to determine the carbon monoxide gas concentration by compensating for the measurement result of the oxygen concentration;
wherein gold or a gold alloy comprising 90 wt % or more gold is used as the sole carbon monoxide sensing material in the carbon monoxide gas measurement sensing electrode.

10. The carbon monoxide gas sensor according to claim 9, wherein a gas diffusion regulating layer is formed on the surface of the carbon monoxide gas measurement sensing electrode.

11. The carbon monoxide gas sensor according to claim 9, wherein both the carbon monoxide gas measurement sensing and reference electrodes are arranged on the same surface of the solid electrolyte.

12. The carbon monoxide gas sensor according to claim 9, further comprising means to cause a constant current to flow between the carbon monoxide gas measurement sensing electrode and the reference electrode and means to measure an electromotive force change caused by the absorption/oxidation of carbon monoxide in the sensing electrode when a constant current is caused to flow between the carbon monoxide gas measurement sensing and reference electrodes, to thereby determine the concentration of carbon monoxide gas.

13. The carbon monoxide gas sensor according to claim 9, further comprising means to maintain a constant voltage between the carbon monoxide gas measurement sensing electrode and the reference electrode and means to measure a current value cause by the oxidation of carbon monoxide gas in the sensing electrode when a constant voltage is maintained between the carbon monoxide gas measurement sensing and reference electrodes, to thereby determine the concentration of carbon monoxide gas.

14. The carbon monoxide gas sensor according to claim 9, wherein the solid electrolyte comprises zirconium oxide and stabilizer.

15. The carbon monoxide gas sensor according to claim 14, wherein the stabilizer included in the solid electrolyte comprises one or more selected from the group consisting of magnesium oxide, calcium oxide, yttrium oxide, cerium oxide, scandium oxide, and rare earth metal oxides.

16. The carbon monoxide gas sensor according to claim 9, wherein the solid electrolyte is capable of being used in the range of 600 to 900° C.

17. The carbon monoxide gas sensor according to claim 9, wherein said sensor further comprising a high temperature pre-treatment portion capable of preheating the measurement gas in the range of 850 to 950° C. before the measurement gas reached the carbon monoxide gas measurement sensing electrode.

18. The carbon monoxide gas sensor according to clam 9, wherein said carbon monoxide gas measurement sensing electrode and said reference electrode are installed facing each other through the solid electrolyte.

19. The carbon monoxide gas sensor according to claim 9, wherein an auxiliary reference electrode for carbon monoxide gas measurement is formed in addition to the carbon monoxide gas measurement sensing and reference electrodes to form a three-electrode structure.

20. A carbon monoxide gas sensor comprising:
a solid electrolyte having an oxygen ion transfer property;
carbon monoxide gas measurement sensing and reference electrodes electrically connected to at least part of the surface of the solid electrolyte;

said carbon monoxide gas measurement sensing electrode either (a) is formed by laying an electrode film on Au or an Au alloy fine particle layer which is disposed on the solid electrolyte or (b) is a cermet electrode comprising gold or a gold alloy and the same material as that of the solid electrolyte;

oxygen measurement sensing and reference electrodes;

said carbon monoxide gas measurement sensing electrode and said reference electrode forming a pair of electrodes; said carbon monoxide gas measurement sensing electrode and said reference electrode being installed facing each other through the solid electrolyte or said carbon monoxide gas measurement sensing electrode and said reference electrode being aligned on same surface of the solid electrolyte; and an oxygen pump cell for controlling an oxygen concentration in a measurement atmosphere;

means for simultaneously measuring the carbon monoxide concentration and the oxygen concentration; and means for compensating the measurement result of the carbon monoxide by the measurement result of the oxygen concentration to thereby determine the carbon monoxide gas concentration;

wherein gold or a gold alloy is used in the carbon monoxide gas measurement sensing electrode.

21. The carbon monoxide gas sensor according to claim 20, wherein an electrode for the oxygen pump cell is made of a metal oxide.

22. The carbon monoxide gas sensor according to claim 20, the carbon monoxide gas measurement sensing electrode is formed by laying an electrode film on Au or an Au alloy fine particle layer which is disposed on the solid electrolyte.

23. The carbon monoxide gas sensor according to claim 20, wherein the carbon monoxide measurement sensing electrode is a cermet electrode comprising gold or a gold alloy and the same material as that of the solid electrolyte.

24. The carbon monoxide gas sensor according to claim 20, wherein a gas diffusion regulating layer is formed on the surface of the carbon monoxide gas measurement sensing electrode.

25. The carbon monoxide gas sensor according to claim 20, wherein both the carbon monoxide gas measurement sensing and reference electrodes are arranged on the same surface of the solid electrolyte.

26. The carbon monoxide gas sensor according to claim 20, further comprising means to cause a constant current to flow between the carbon monoxide gas measurement sensing electrode and the reference electrode and means to measure an electromotive force change caused by the adsorption/oxidization of carbon monoxide in the carbon monoxide gas measurement sensing electrode when a constant current is caused to flow between the carbon monoxide gas measurement sensing and reference electrodes, to thereby determine the concentration of carbon monoxide gas.

27. The carbon monoxide gas sensor according to claim 20, further comprising means to maintain a constant voltage between the carbon monoxide gas measurement sensing electrode and the reference electrode and means to measure a current value caused by the oxidization of carbon monoxide gas in the carbon monoxide gas measurement sensing electrode when a constant voltage is maintained between the carbon monoxide gas measurement sensing and reference electrodes, to thereby determine the concentration of carbon monoxide gas.

28. The carbon monoxide gas sensor according to claim 20, wherein the solid electrolyte comprises zirconium oxide and stabilizer.

29. The carbon monoxide gas sensor according to claim 28, wherein the stabilizer included in the solid electrolyte comprises one or more selected from the group consisting of magnesium oxide, calcium oxide, yttrium oxide, cerium oxide, scandium oxide, and rare earth metal oxides.

30. The carbon monoxide gas sensor according to claim 20, wherein the solid electrolyte is capable of being used in the range of 600 to 900° C.

31. The carbon monoxide gas sensor according to claim 20, wherein said sensor further comprises a high temperature pre-treatment portion capable of preheating the measurement gas in the range of 850 to 950° C. before the measurement gas reaches the carbon monoxide gas treatment sensing electrode.

32. The carbon monoxide gas sensor according to claim 20, wherein said carbon monoxide gas measurement sensing electrode and said reference electrode are installed facing each other through the solid electrolyte.

33. The carbon monoxide gas sensor according to claim 20, wherein an auxiliary reference electrode for carbon monoxide gas measurement is formed in addition to the carbon monoxide gas measurement sensing and reference electrodes to form a three-electrode structure.

* * * * *